United States Patent [19]
Rocco

[11] Patent Number: 5,581,838
[45] Date of Patent: Dec. 10, 1996

[54] ARTICULATING TOOTHBRUSH ASSEMBLY

[76] Inventor: Anthony C. Rocco, 3 Spruceton St., Selden, N.Y. 11784

[21] Appl. No.: 418,552

[22] Filed: Apr. 7, 1995

[51] Int. Cl.⁶ ............................ A46B 9/04; F16C 11/04
[52] U.S. Cl. ........................ 15/110; 15/105; 15/144.1; 15/145; 15/167.1; 15/172; 15/176.1; 132/309; 132/321; 132/323; 403/91; 403/99; 403/329; 601/141
[58] Field of Search ......................... 15/105, 110, 144.1, 15/145, 167.1, 172, 176.1; 132/308–311, 321, 323–325; 403/91, 92, 97–99, 326, 329; 601/139, 141

[56] References Cited

U.S. PATENT DOCUMENTS

| | | |
|---|---|---|
| 2,517,045 | 8/1950 | Soule . |
| 2,657,412 | 11/1953 | Carlson ..................... 15/185 |
| 2,668,973 | 2/1954 | Glaza et al. . |
| 2,679,657 | 6/1954 | Krueger ..................... 15/172 |
| 2,823,404 | 2/1958 | Hyman ....................... 15/145 |
| 3,103,680 | 9/1963 | Krichmar ................... 15/167.1 |
| 3,868,742 | 3/1975 | Brenner ..................... 15/172 |
| 3,879,139 | 4/1975 | Dahl et al. . |
| 4,020,521 | 5/1977 | Velasquez .................. 15/172 |
| 4,128,910 | 12/1978 | Nakata et al. ............. 15/110 |
| 4,227,276 | 10/1980 | Ginsburg et al. . |
| 4,362,174 | 12/1982 | Baker et al. . |
| 4,582,445 | 4/1986 | Warshawsky .............. 403/97 |
| 4,731,896 | 3/1988 | de La Tour ................ 15/106 |
| 4,780,924 | 11/1988 | Hansen et al. ............ 15/176.1 |
| 4,829,621 | 5/1989 | Phenegar ................... 15/172 |
| 4,890,349 | 1/1990 | Nitzsche .................... 15/167.1 |
| 4,890,732 | 1/1990 | Shackelford .............. 206/362.1 |
| 4,905,946 | 3/1990 | Wang ......................... 403/92 |
| 4,929,113 | 5/1990 | Sheu .......................... 403/91 |
| 5,005,246 | 4/1991 | Yen-Hui ..................... 15/111 |
| 5,010,906 | 4/1991 | Preciutti .................... 132/323 |
| 5,033,154 | 7/1991 | Marchard et al. ......... 15/167.1 |
| 5,044,948 | 9/1991 | Vance, Sr. et al. . |
| 5,109,563 | 5/1992 | Lemon et al. ............. 15/167.1 |
| 5,144,712 | 9/1992 | Hansel et al. ............. 15/167.1 |
| 5,165,135 | 11/1992 | Su .............................. 15/167.1 |
| 5,263,507 | 11/1993 | Chuang ..................... 403/97 |
| 5,442,831 | 8/1995 | Yamada ..................... 15/167.1 |

*Primary Examiner*—Mark Spisich
*Attorney, Agent, or Firm*—Dilworth & Barrese

[57] ABSTRACT

A toothbrush assembly is disclosed which includes an articulating head portion for releasable supporting a brushhead, and which is configured to releasably mount a plurality of interchangeable dental accessory tools. A spring biased actuation member having a plurality of sprockets associated therewith is provided for effectuating incremental articulated movements of the brushhead supporting portion with respect to the handle of the toothbrush assembly to position the brushhead in a desired angular orientation.

15 Claims, 5 Drawing Sheets

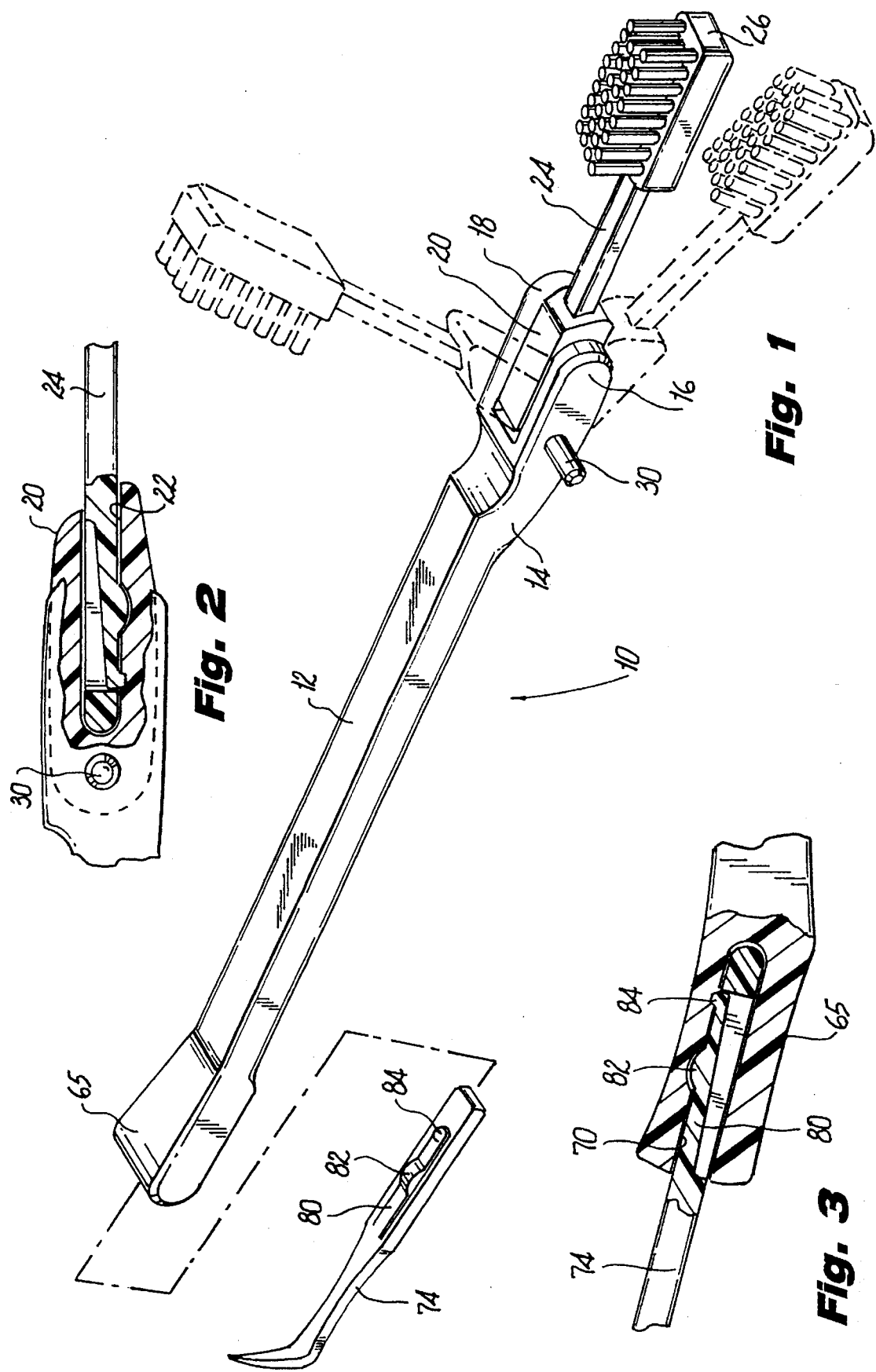

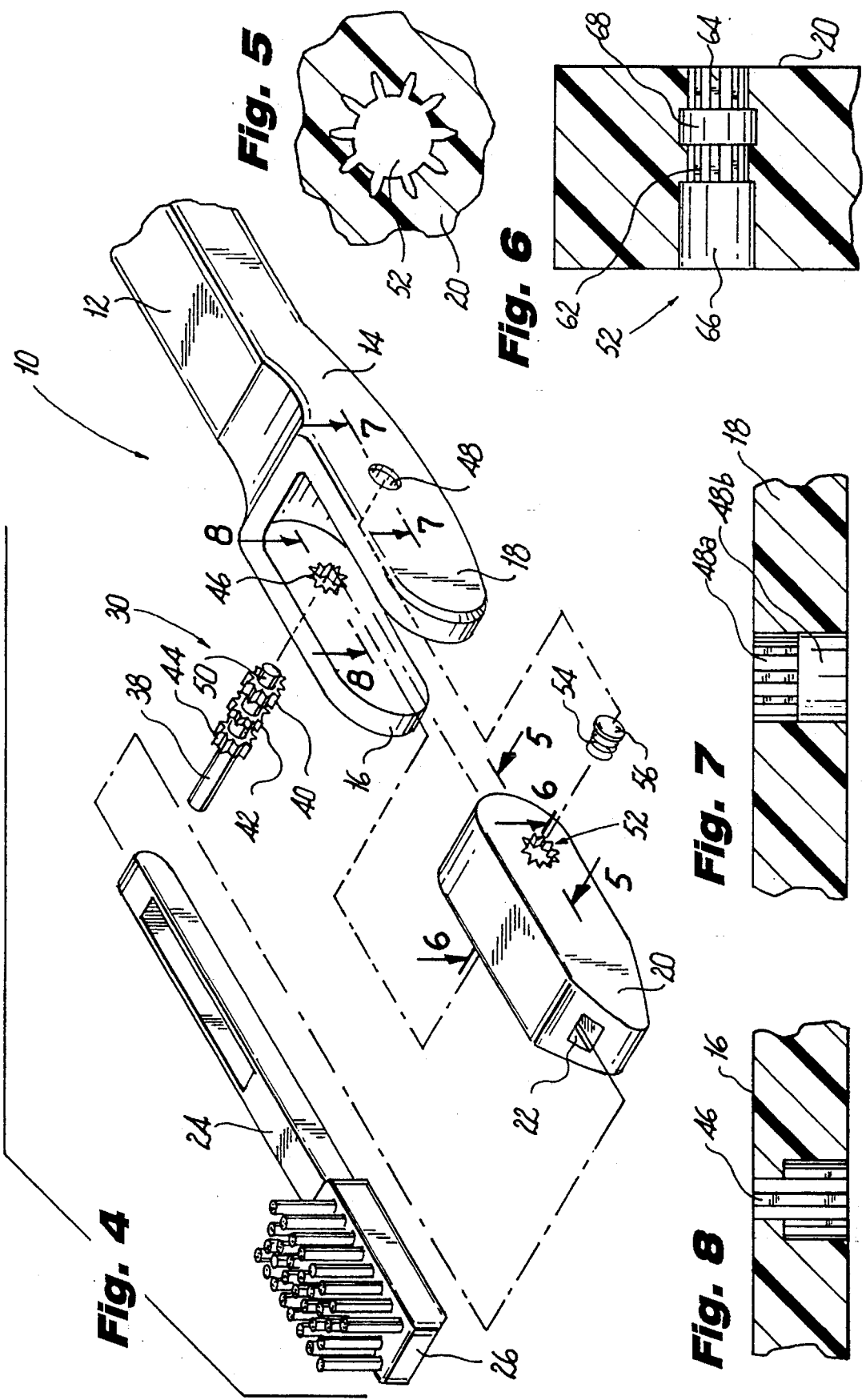

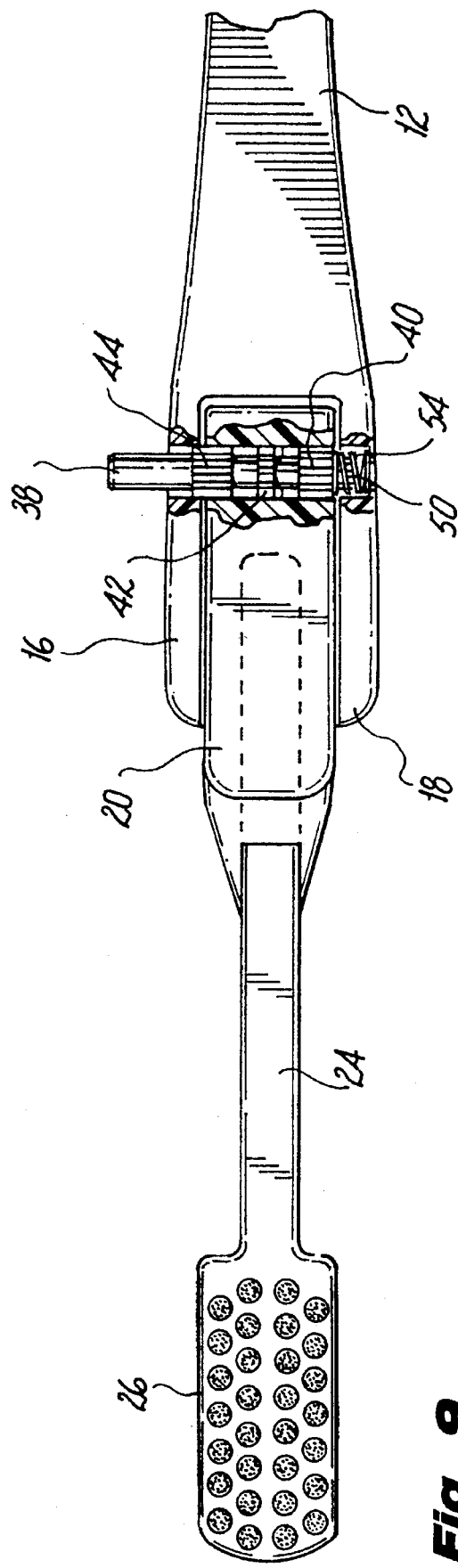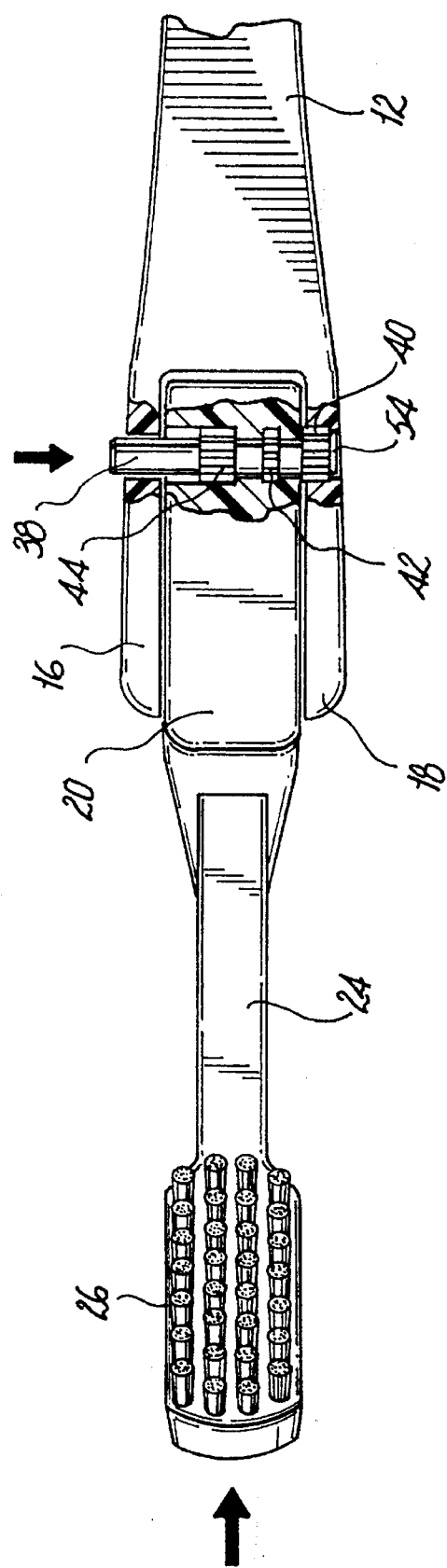

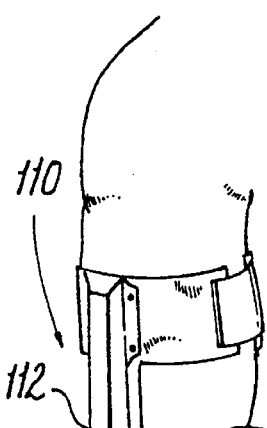
Fig. 14
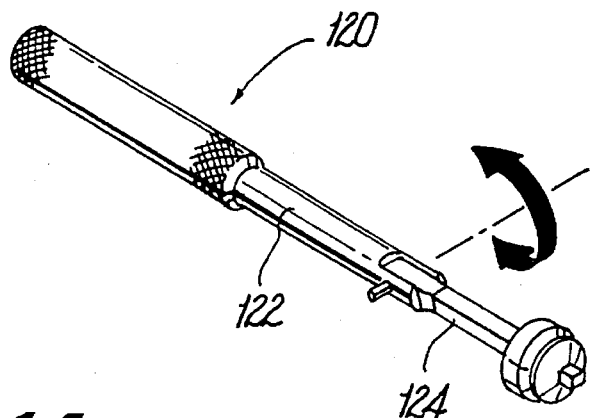
Fig. 15
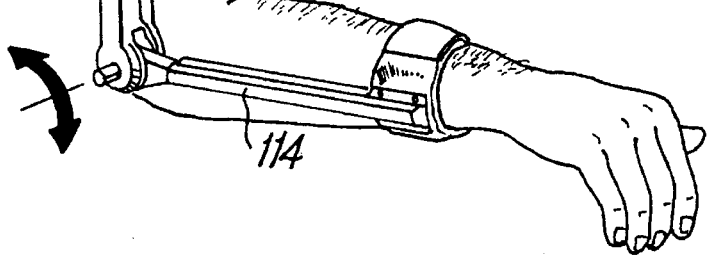
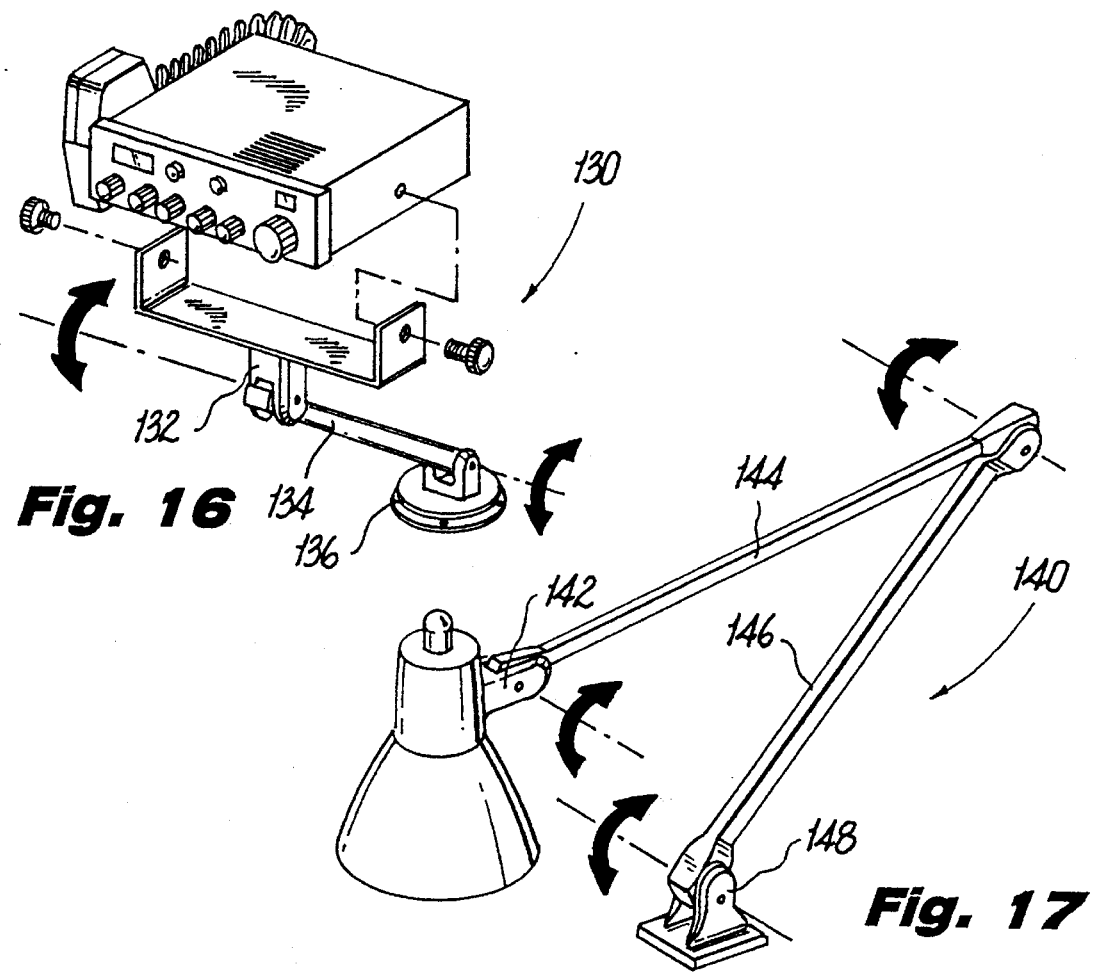
Fig. 16
Fig. 17

5,581,838

ARTICULATING TOOTHBRUSH ASSEMBLY

BACKGROUND OF THE INVENTION

1. Technical Field

The subject invention is directed to an articulating structural assembly, and more particularly, to a toothbrush assembly having an articulating brushhead that is selectively movable into a plurality of angular orientations with respect to the toothbrush handle.

2. Background of the Related Art

Proper oral hygiene requires that when brushing one's teeth all parts of the mouth are accessed so that each tooth is adequately cleaned. In the past, a variety of toothbrushes having pivoting brushheads were introduced in an attempt to provide a suitable mechanism to access remote areas of the mouth when brushing. For example, U.S. Pat. No. 4,731,896 to de La Tour discloses a toothbrush having an adjustable brushhead portion. The toothbrush has a jointed section with an integral gear and socket mechanism configured to facilitate indexed movement of the brushhead relative to the toothbrush handle. Although constructed in a useful manner, the entire de La Tour toothbrush must be discarded when the bristles have become worn. Other examples of toothbrushes having articulating brushheads are disclosed in U.S. Pat. No. 5,033,154 and U.S. Pat. No. 5,165,135.

Proper oral hygiene also requires the use of such items as dental floss to remove debris from areas between the teeth and gums that are not easily reached with a toothbrush, and gum massagers to stimulate the gums and enhance blood flow and the growth of healthy tissue. Often these items are maintained in a location separate from a toothbrush. However, toothbrushes have been devised which incorporate oral hygiene tools in their handles, as shown for example, in U.S. Pat. No. 5,010,906 to Preciutti.

In view of the prior art, it would be beneficial to provide an articulating toothbrush assembly having a removable brushhead that can be easily replaced when it becomes worn, and which is configured to support a plurality of interchangeable dental appliances that can be employed to improve the overall dental hygiene of the user.

SUMMARY OF THE INVENTION

The subject invention is directed to an articulating structural assembly having first and second relatively articulatable structural portions. The first structural portion includes a yoke section having first and second opposed yoke arms each having a toothed aperture extending at least partially therethrough, and the second structural portion has a shank section which is dimensioned and configured to extend between the opposed yoke arms and which has a bore extending therethrough that includes two spaced apart annular toothed areas and two spaced apart annular race areas formed therein.

An axle member extends through the toothed apertures of the yoke arms and the bore of the shank section and has first, second, and third spaced apart sprockets provided thereon which facilitate incremental articulated movements of the second structural portion with respect to the first structural portion. Means are disposed within the second yoke arm for biasing the axle member into an engaged position wherein the first sprocket is engaged within the toothed aperture of the first yoke arm and the second and third sprockets are disposed in the spaced apart toothed areas of the bore.

In use, movement of the axle member against the bias of the biasing means moves the axle member from the engaged position to a disengaged position wherein the first and second sprockets are disposed within the spaced apart race areas of the bore and the third sprocket is engaged in the toothed aperture of the second yoke arm to facilitate articulated movement of the second structural portion relative to the first structural portion.

In a preferred embodiment of the subject invention, the structural assembly is configured as an articulating toothbrush assembly with the first structural portion defining a handle or body portion and the second structural portion defining a supporting structure for the brushhead. The front end section of the body portion defines a yoke having first and second opposed yoke arms each having a toothed aperture extending at least partially therethrough. The brushhead supporting portion is dimensioned to extend between the opposed yoke arms and has a bore extending therethrough which has two spaced apart annular toothed areas and two spaced apart annular race areas formed therein.

An axle member extends through the toothed apertures of the yoke section and the bore of the brushhead supporting portion and has first, second, and third spaced apart sprockets formed thereon for interacting with those structures. A spring is positioned within the toothed aperture of the second yoke arm for biasing the axle member into an engaged position wherein the first sprocket is engaged within the toothed aperture of the first yoke arm and the second and third sprockets are engaged within the toothed areas of the bore.

In use, movement of the axle member against the bias of the spring translates the axle member from the engaged position to a disengaged position wherein the first and second sprockets are disposed within the annular race areas of the bore and the third sprocket is engaged in the toothed aperture of the second yoke arm to facilitate articulated movement of the brushhead supporting portion relative to the body portion of the toothbrush assembly.

These and other features of the subject invention will become more readily apparent from the following detailed description of the invention taken in conjunction with the drawings.

BRIEF DESCRIPTION OF THE DRAWINGS

So that one skilled in the art to which the subject invention appertains will better understand how to make and use the articulating toothbrush assembly of the subject invention, preferred embodiments thereof will be described hereinbelow with reference to the drawings wherein:

FIG. 1 is a perspective view of an articulating toothbrush assembly constructed in accordance with a preferred embodiment of the subject invention with the brushhead shown in a plurality of angular orientations;

FIG. 2 is a side elevational view in partial cross-section of the head portion of the toothbrush assembly illustrating the mechanism which releasably secures the brushhead to the articulating portion of the toothbrush assembly;

FIG. 3 is a side elevational view in partial cross-section of the rear end of the toothbrush handle illustrating the mechanism which releasably secures the tool members to the toothbrush assembly;

FIG. 4 is an exploded perspective view of the front end portion of the toothbrush assembly illustrated in FIG. 1 with each of the parts separated for ease of illustration;

FIG. 5 is a cross-sectional view taken along line 5—5 of FIG. 4 illustrating a toothed area of the bore which extends through the head portion of the toothbrush assembly;

FIG. 6 is a cross-sectional view taken along line 6—6 of FIG. 4 illustrating the bore which extends through the head portion of the toothbrush assembly;

FIG. 7 is a cross-sectional view taken along lines 7—7 of FIG. 4 illustrating the partially toothed aperture formed in the second yoke arm at the front end of the body portion of the toothbrush assembly;

FIG. 8 is a cross-sectional view taken along line 8—8 of FIG. 4 illustrating the toothed aperture which extends through the first yoke arm at the front end of the body portion of the toothbrush assembly;

FIG. 9 is a top plan view of the toothbrush assembly of FIG. 1 with the brushhead portion disposed in a non-articulated position and the sprocketed axle biased into a locked position;

FIG. 10 is a top plan view of the toothbrush assembly of FIG. 1 with the brushhead portion disposed in an articulated position and the sprocketed axle moved into an unlocked position to permit movement of the brushhead portion relative to the handle portion;

FIG. 14 is a perspective view of an arm cast which incorporates the articulating structural assembly of the subject invention;

FIG. 15 is a perspective view of a ratchet wrench which incorporates the articulating structural assembly of the subject invention;

FIG. 16 is a perspective view of a radio stand which incorporates the articulating structural assembly of the subject invention at two separate locations to facilitate relative movement of three structural portions of the radio stand; and FIG. 17 is a perspective view of a desk lamp which incorporates the articulating structural assembly of the subject invention at three separate locations to facilitate relative movement of four structural portions of the desk lamp.

DETAILED DESCRIPTION OF PREFERRED EMBODIMENTS

Figure 11:
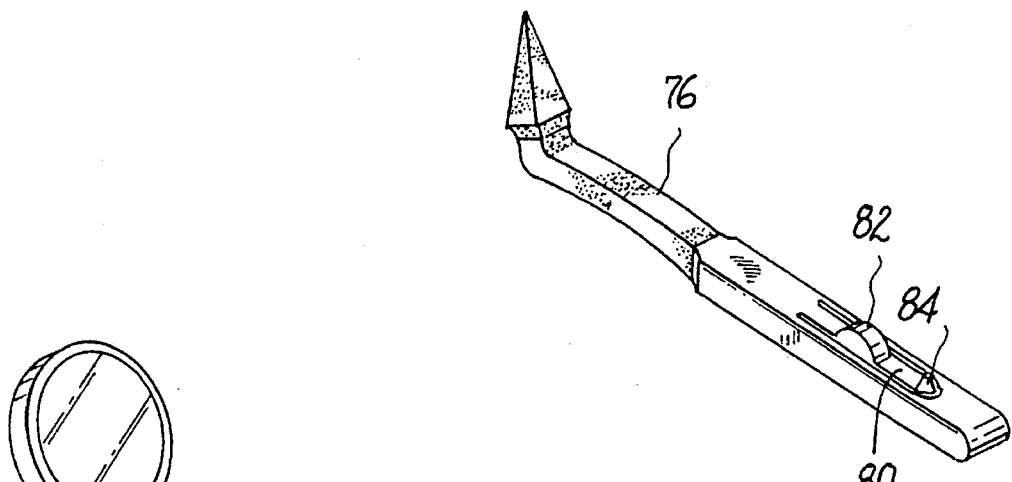
FIG. 11 is a perspective view of a gum massager having an engagement mechanism for releasable securement in the rear end of the toothbrush handle.

Referring now to the drawings wherein like reference numerals identify similar structural elements of the subject invention, there is illustrated in FIG. 1 an articulating toothbrush assembly constructed in accordance with a preferred embodiment of the subject invention and designated generally by reference numeral 10. Toothbrush assembly 10 is particularly adapted to promote good oral hygiene by providing a unique brushhead that can be oriented into a plurality of angular positions so as to increase access to remote areas of the mouth that are often difficult to reach with conventional toothbrushes. Moreover, the articulating brushhead may be particularly useful for persons who are handicapped or disabled and who find difficulty in orienting a conventional toothbrush.

Referring to FIG. 1, toothbrush assembly 10 includes an elongated body 12 which defines an ergonomically configured handle along a major portion thereof and a yoke section 14 at the front end thereof. Yoke section 14 has two opposed yoke arms 16 and 18 which operatively support the brushhead retaining section 20 of toothbrush assembly 10. Retaining section 20 has a reception port 22 formed therein for receiving the support shaft 24 of brushhead 26. As best seen in FIG. 2, reception port 22 and support shaft 24 have complementary engagement structures which interact to releasably secure the brushhead 26 in retaining section 20. Thus, when the bristles of the brushhead become worn, it can be easily removed from retaining section 20 and replaced with a new brushhead.

Referring again to FIG. 1, toothbrush assembly 10 also includes an actuation member 30 which is operatively associated with the yoke section 14 of body 12 and the retaining section 20 for effectuating the articulated movements of the brushhead 26 with respect to the handle defined by body 12. As best seen in FIG. 4, actuation member 30 is defined by an axle shaft 38 having three spaced apart sprockets provided thereon designated by reference numerals 40, 42, and 44. Each sprocket has a plurality of annularly disposed gear teeth which are configured to interact with complementary toothed engagement areas formed within the yoke arms 16 and 18 of yoke section 14 of the retaining section 20 of toothbrush assembly 10.

In particular, as shown in FIG. 8, yoke arm 16 has a partially toothed aperture 46 formed therein which interacts with the innermost sprocket 44 of axle shaft 38, and as shown in FIG. 7, yoke arm 18 is formed with a partially toothed aperture 48 for interacting with the stub shaft section 50 of axle shaft 38 and the outermost sprocket 40 of axle shaft 38. Aperture 48 has a toothed area 48a and a recessed cavity 48b. A coiled biasing spring 54 resides in the recessed cavity 48b and is supported therein by the stub portion 50 of axle shaft 38. An end cap 56 fits within the recessed cavity 48b to enclose coiled spring 54 therein.

Referring to FIG. 6, a bore 52 extends through brushhead retaining portion 20 and includes two spaced apart annular toothed areas 62 and 64, and two spaced apart annular race areas 66 and 68 which facilitate free-movement of retaining portion 20. The toothed areas cooperate with the sprockets on axle shaft 38 to maintain brushhead retaining portion 20 in a desired angular orientation with respect to body 12, and the race areas cooperate with the sprockets to permit relative pivotal movement of retaining portion 20 with respect to body 12. This interaction is best illustrated in FIGS. 9 and 10.

Referring to FIG. 9, when actuation member 30 is biased outwardly by coiled spring 54, sprocket 40 engages the toothed area 48a in yoke arm 18 and the toothed area 64 in retaining portion 20, sprocket 42 engages the toothed area 62 in retaining portion 20, and sprocket 44 engages the toothed aperture 46 formed in yoke arm 16. At such a time, retaining portion 20 is locked against rotation and toothbrush assembly 10 may be used to brush one's teeth. When it becomes desirable to orient brushhead 26 in an articulated position, actuation member 30 is depressed against the bias of coiled spring 54. Then, as shown in FIG. 10, sprocket 44 disengages toothed aperture 46 and moves into race area 66, sprocket 42 disengages toothed area 62 and moves into race area 68, and sprocket 40 moves from toothed area 64 into the toothed section 48a of aperture 48. Thereupon, retaining portion 20 can be moved into a desired angular orientation. Once the proper position has been reached, release of actuation member 30 will permit spring 54 to urge axle shaft

38 into its normally locked position illustrated in FIG. 9 and the toothbrush can be utilized once again.

The number of articulated positions of the brushhead will depend upon the number of teeth provided on the sprockets of axle shaft 38. Each sprocket has the same number of teeth formed thereon, but it is envisioned that the number of teeth may vary from as few as ten to as many as thirty. In a preferred embodiment of the subject invention, twenty-six teeth are provided on each sprocket of axle shaft 38 so that the brushhead retaining portion 20 can be oriented into an incremental position every 13.85°.

Figure 12:
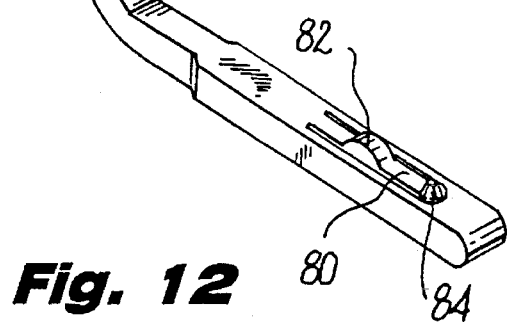
FIG. 12 is a perspective view of a dental mirror having an engagement mechanism for releasable securement in the rear end of the toothbrush handle.
Figure 13:
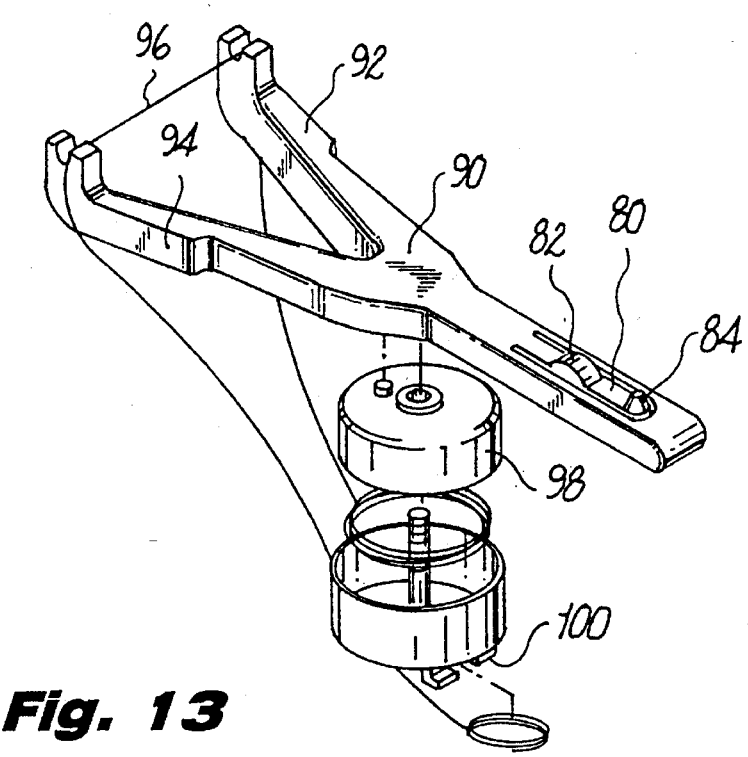
FIG. 13 is a perspective view, with parts separated for ease of illustration, of a dental floss dispenser with a yoke mount having an engagement mechanism for releasable securement in the rear end of the toothbrush handle.

As best seen in FIGS. 1 and 3, the rear end 65 of toothbrush body 12 includes a reception port 70 for receiving the support shaft of a removable dental accessory tool, such as, for example, dental pick 74. Other dental accessory tools are also provided. For example, a gum massager 76 is illustrated in FIG. 11, an angled dental mirror 78 is illustrated in FIG. 12, and a dental floss dispensing unit is illustrated in FIG. 13. Each of the dental accessory tools has engagement structure associated therewith in the form of an integral living hinge 80 which has a rounded protuberance 82 and a conical detent 84 provided thereon for engaging complementary structures formed within reception port 70, as illustrated in FIG. 3. As shown in FIG. 2, similar engagement structures are provided on the support shaft 24 of brushhead 26. Thus, if it becomes desirable to employ two different dental accessories, one can be engaged in the brushhead retaining portion, and the other in the rear end of the handle.

Referring to FIG. 13, dental floss dispensing unit includes a yoke assembly 90 having two bifurcated arms 92 and 94 which are configured to support a strand of dental floss 96. Dental floss is stored within a cylindrical chamber 98 that is fastened to yoke assembly 90. An anchoring fixture 100 is provided on chamber 98 for securing the free end of the dental floss.

Turning now to FIGS. 14–17, there are illustrated various tools and appliances that employ the articulating structural assembly of the subject invention to facilitate the relative articulated movement of at least two structural members. Moreover, it is envisioned that the sprocketed axle 38 which defines the actuation member 30 of toothbrush assembly 10 can be utilized to facilitate the relative articulated movements of any two structural elements which form part of a tool or appliance. For example, an arm cast 110 having two structural elements 112 and 114 which employ the articulation assembly of the subject invention is illustrated in FIG. 14, and an articulated ratchet wrench 120 having elements 122 and 124 employing the same structural assembly is shown in FIG. 15. As illustrated, the articulation assemblies each include one member having a yoke section and one member which has a shank dimensioned to extend between the arms of the yoke.

A radio stand 130 having three structural elements 132, 134, and 136 and employing the articulation assembly of the subject invention at two separate locations is illustrated in FIG. 16. A desk lamp 140 which employs the articulation assembly of the subject invention at three separate locations to control the relative incremental movements of four structural portions 142–148 is illustrated in FIG. 17. Other applications are also envisioned for the articulation assembly of the subject invention, such as, for example, an articulating head rest for automobile seats that can be easily positioned and locked in a desired angular orientation.

Although the subject invention has been described with respect to preferred embodiments, it will be readily apparent to those having ordinary skill in the art to which it appertains that changes and modifications may be made thereto without departing from the spirit or scope of the subject invention as defined by the appended claims.

What is claimed is:

1. An articulating toothbrush assembly which comprises:
    a) an elongated body portion having front and rear end sections, the front end section defining a yoke having first and second opposed yoke arms each having a toothed aperture extending at least partially therethrough;
    b) a head portion dimensioned to extend between the opposed yoke arms and configured to support a brush member and having a bore extending therethrough including first and second spaced apart annular toothed areas and first and second spaced apart annular race areas;
    c) an axle shaft extending through the toothed apertures of the yoke arms and the toothed bore of the head portion and having first, second and third spaced apart sprockets provided thereon for facilitating incremental articulation of the head portion with respect to the body portion; and
    d) means positioned within the toothed aperture of the second yoke arm for biasing the axle shaft into an engaged position wherein the first sprocket is engaged in the toothed aperture of the first yoke arm, the second sprocket is engaged within the first toothed area of the bore, and the third sprocket is engaged within the second toothed area of the bore and the toothed aperture in the second yoke arm, whereby movement of the axle shaft against the bias of the biasing means moves the axle shaft from the engaged position to a disengaged position wherein the first and second sprockets are disposed within the first and second race areas of the bore and the third sprocket is engaged in the toothed aperture in the second yoke arm to permit articulated movement of the head portion of the toothbrush assembly relative to the body portion of the toothbrush assembly.

2. A toothbrush assembly as recited in claim 1, wherein a reception port is formed in the head portion for releasably receiving a selected one of the brush member, and a plurality of interchangeable accessory tool members.

3. A toothbrush assembly as recited in claim 2, wherein the brush member has an extension shaft which extends into the reception port and includes an integral engagement mechanism for releasably engaging an internal surface of the reception port.

4. A toothbrush assembly as recited in claim 1, wherein an auxiliary reception port is provided at the rear end of the body portion for releasably receiving an accessory tool member.

5. A toothbrush assembly as recited in claim 4, wherein the accessory tool member has an extension shaft which extends into the auxiliary reception port and includes an integral engagement mechanism for releasably engaging an internal surface of the auxiliary reception port.

6. A toothbrush assembly as recited in claim 4, wherein the accessory tool member is selected from the group consisting of a dental pick, a dental mirror, a gum massager, and a dental floss dispenser.

7. A toothbrush assembly as recited in claim 1, wherein the biasing means comprises a coiled compression spring and an end cap is provided for retaining the spring in the toothed aperture of the second yoke arm.

8. A toothbrush assembly as recited in claim 1, wherein each of the sprockets provided on the axle shaft have the same number of teeth formed thereon.

9. A toothbrush assembly as recited in claim 8, wherein each of the sprockets have between ten and thirty teeth formed thereon.

10. A toothbrush assembly as recited in claim 9, wherein each of the sprockets have twenty-six teeth formed thereon.

11. An articulating structural assembly which comprises:
   a) an first structural portion including a yoke section having first and second opposed yoke arms each having a toothed aperture extending at least partially therethrough;
   b) a second structural portion having a shank section dimensioned and configured to extend between the opposed yoke arms and having a bore extending therethrough which includes first and second spaced apart annular toothed areas and first and second spaced apart annular race areas;
   c) an axle shaft extending through the toothed apertures and the bore and having first, second, and third spaced apart sprockets provided thereon for facilitating incremental articulated movements of the second structural portion with respect to the first structural portion; and
   d) means positioned within the second yoke arm for biasing the axle shaft into an engaged position wherein the first sprocket is engaged in the toothed aperture of the first yoke arm, the second sprocket is engaged in the first toothed area of the bore, and the third sprocket is engaged in the second toothed area of the bore and the toothed aperture in the second yoke arm, whereby movement of the axle shaft against the bias of the biasing means moves the axle shaft from the engaged position to a disengaged position wherein the first and second sprockets are disposed within the first and second race areas of the bore and the third sprocket is engaged in the toothed aperture of the second yoke arm to facilitate articulated movement of the second structural portion relative to the first structural portion.

12. A structural assembly as recited in claim 11, wherein the biasing means comprises a coiled compression spring and an end cap is provided for retaining the compression spring in the toothed aperture of the second yoke arm.

13. A structural assembly as recited in claim 11, wherein each sprocket has a plurality of teeth formed thereon.

14. A structural assembly as recited in claim 13, wherein each of the sprockets provided on the axle shaft have the same number of teeth formed thereon.

15. A structural assembly as recited in claim 13, wherein each of the sprockets have between ten and thirty teeth formed thereon.

* * * * *